United States Patent [19]

Bindra

[11] 4,085,213

[45] Apr. 18, 1978

[54] TETRAZOLO[A]QUINAZOL-5-ONES ANTIALLERGY AND ANTIULCER AGENTS

[75] Inventor: Jasjit S. Bindra, Groton, Conn.

[73] Assignee: Pfizer Inc., New York, N.Y.

[21] Appl. No.: 753,856

[22] Filed: Dec. 23, 1976

Related U.S. Application Data

[63] Continuation-in-part of Ser. No. 653,250, Jan. 28, 1976, abandoned, which is a continuation-in-part of Ser. No. 594,765, Jul. 10, 1975, abandoned.

[51] Int. Cl.² .................. A61K 31/305; C07D 487/04
[52] U.S. Cl. ............................ 424/251; 260/256.4 F; 260/251 QA
[58] Field of Search ................. 260/256.4 F; 424/251

[56] References Cited

U.S. PATENT DOCUMENTS

| | | | |
|---|---|---|---|
| 3,714,354 | 1/1973 | Stam | 260/251 QA |
| 3,835,137 | 9/1974 | Wagner | 260/256.4 F |
| 3,838,126 | 9/1974 | Wagner | 260/256.4 F |
| 4,020,083 | 4/1977 | Kathawala | 260/256.4 F |

OTHER PUBLICATIONS

Goncharova, et al., "Chemical Abstracts", vol. 60, 1963, col. 1743d.
Vereshchagina, et al., "Chemical Abstracts", vol. 61, 1964, col. 8307f.

*Primary Examiner*—Donald G. Daus
*Assistant Examiner*—James H. Turnipseed
*Attorney, Agent, or Firm*—Connolly and Hutz

[57] ABSTRACT

A series of tetrazolo[a]quinazol-5-ones, methods for their production and use as antiallergy agents and antiulcer agents.

3 Claims, No Drawings

TETRAZOLO[A]QUINAZOL-5-ONES ANTIALLERGY AND ANTIULCER AGENTS

CROSS-REFERENCE TO RELATED APPLICATIONS

This application is a continuation-in-part of application Ser. No. 653,250, filed Jan. 28, 1976, which in turn is a continuation-in-part of application Ser. No. 594,765, filed July 10, 1975 both now abandoned.

BACKGROUND OF THE INVENTION

1. Field of the Invention

This invention relates to tetrazolo[a]quinazol-5-one and derivatives thereof and to their use for the control of peptic ulcers and allergic reactions.

2. Description of the Prior Art

Tetrazolo[a]quinazol-5-one, the parent compound of the series of compounds described herein is described by Postovskii et al., Zhur. Obshchei Khim., 33, 2334-2341 (1963) [C.A. 59, 13987a]. Several 4-substituted tetrazolo[a]quinazol-5-ones are described by Vereshchagina et al., Zhur. Obshchei. Khim., 34, 1745-8 (1964) [C.A. 61, 8307-8]. However, these references do not report any utility for the compounds. Neither tetrazolo[a]quinazol-5-one or 7-methoxy-8-n-propoxytetrazolo[a]quinazol-5-one showed bronchodilator activity when tested in guinea pigs by the procedure of Van Arman et al., J. Pharm. Exptl. Therap., 153, 90-7 (1961).

A series of tetrazolo(1,5-c)quinazolin-5(6H)-ones useful as bronchodilators is described in U.S. Pat. No. 3,838,126, issued Sept. 24, 1974.

Allergic reactions, the symptoms resulting from an antigen-antibody interaction, manifest themselves in a wide variety of ways and in different organs and tissues. Common allergic disorders, for example, are allergic rhinitis, a condition characterized by seasonal or perennial sneezing, running nose, nasal congestion, with itching and congestion of eyes; hay fever, a variety of allergic rhinitis that results from hypersensitivity to grass pollens; and bronchial asthma, one of the most disabling and debilitating of allergic reactions, a disease characterized by hyper-reactivity of the bronchi on exposure to various immunogenic or nonimmunogenic stimuli, resulting in bronchospasms with wheezing, short-lived paroxysms and widespread constriction of airway passages. The mechanical obstruction to airflow in airways is generally reversed by the use of bronchodilators, which provide symptomatic relief. In contrast, antiallergy agents prevent the release of mediators of anaphylaxis from tissue stores to preclude elicitation of bronchoconstriction by the mediators.

Recently, Cos and co-workers, Adv. in Drug Res., 5, 115 (1970), described the pharmacology of one such agent, disodium cromoglycate [1,3-bis(2-carboxycromon-5-yloxy)-2-hydroxypropane, Intal]. It is not a bronchodilator, but mediates its therapeutic effects by a unique mechanism of action involving inhibition of release of mediators of anaphylaxis and is administered prophylactically. It suffers from lack of oral efficacy and, for optimum results, is administered by inhalation as a solid inhalant. Further, although it is effective against anaphylaxis due to immunoglobulin E (IgE), it is effective against anaphylaxis due to immunoglobulin G (IgG) only at high doses (60-70% protection at 100 and 300 mg./kg.).

Although the aforementioned agents represent outstanding contributions toward the treatment of asthma, many of them exert the undesired side effect of cardiac stimulation.

Chronic gastric and duodenal ulcers, collectively known as peptic ulcers, are a common affliction for which a variety of treatments have been developed. The treatment depends upon the severity of the ulcer and may range from dietary and medical (drug) treatment to surgery. A wide variety of drugs have been used to treat ulcers; the most recent of which to gain widespread attention is carbenoxolone sodium, the disodium salt of the hemisuccinate of glycyrrhetinic acid. It is reported to prevent formation of and to accelerate healing of gastric ulcers in animals, including humans ("Carbenoxolone Sodium: a Symposium", J. M. Robson and F. M. Sullivan, Eds., Butterworths, London, 1968). However, its use is accompanied by undesirable aldosterone-like side effects, such as marked antidiuretic and sodium-retaining activity, and oftentimes, potassium loss, such that continued therapy with this agent often leads to hypertension, muscle weakness and, ultimately, congestive heart failure.

Carbenoxolone sodium is almost wholly absorbed in the stomach and is not effective against duodenal ulcers except when administered as a specially formulated capsule which enables its transport to the desired site.

A more effective treatment of peptic ulcers is, therefore, desirable. One which will effectively act upon ulcers in the duodenum, as well as upon gastric ulcers, without the need of special formulation and minimizes the aldosterone-like side effects of carbenoxolone is especially desirable.

SUMMARY OF THE INVENTION

It has now been found that tetrazolo[a]quinazol-5-ones of the formula

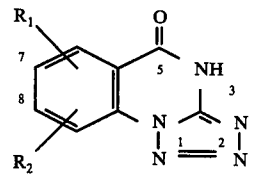

wherein each of $R_1$ and $R_2$ is selected from the group consisting of hydrogen, alkyl having from one to four carbon atoms, alkoxy having from one to four carbon atoms, alkanoyloxy having from one to four carbon atoms, benzyloxy, hydroxy, trifluoromethyl, sulfonamido and halo; and $R_1$ and $R_2$ when taken together are alkylenedioxy and are selected from the group consisting of methylenedioxy and ethylenedioxy, are valuable antiallergy agents; that is, agents which inhibit the release of mediators of anaphylaxis, in mammals, including man, and in this way preclude elicitation of bronchoconstriction by the mediators. They are, in contrast to Intal, of practical value against both IgG and IgE mediated anaphylaxis via the oral, intranasal and intraperitoneal routes of administration, and by inhalation. Additionally, they are effective antiulcer agents which require no special formulation for the treatment of peptic ulcers.

Compounds of the above formula, except for that wherein each of $R_1$ and $R_2$ is hydrogen, are new compounds.

Compounds of the above formula of special interest because of their significant oral activity in the PCA test against both IgG and IgE are those wherein each of $R_1$ and $R_2$ is lower alkoxy having from one to four carbon atoms and particularly those wherein $R_1$ and $R_2$ are located at the 7- and 8-positions of the molecule.

Compounds of formula I wherein $R_1$ and/or $R_2$ are benzyloxy are intermediates for preparation of compounds wherein $R_1$ and/or $R_2$ is hydroxy or alkanoyloxy.

The effectiveness of these compounds as antiulcer agents is determined by the stressed rat assay described below. The antiallergy property of the compounds of this invention is evaluated by the passive cutaneous anaphylaxis (PCA) test (Ovary, *J. Immun.* 81, 355, 1958). In the PCA test normal animals are injected intradermally (i.d.) with antibodies contained in serum obtained from actively sensitized animals. The animals are then challenged intravenously with antigen mixed with a dye such as Evans' Blue. The increased capillary permeability caused by the antigen-antibody reaction causes the dye to leak from the site of the antibody injection. The test animals are then asphyxiated and the intensity of the reaction determined by measuring the diameter and intensity of the blue coloration on the inner surface of the animals' skin.

DETAILED DESCRIPTION OF THE INVENTION

The compounds of this invention are conveniently prepared by the reaction of a metal azide, preferably an alkali metal azide, with the appropriate 2-chloro-4(3H)quinazolinone in about equimolar quantities. In ordinary practice, however, it is preferred to use an excess, generally 5-20% excess, of the metal azide to achieve maximum conversion of the 2-chloro-4(3H)quinazolinone to the azide.

The reaction is carried out in a suitable solvent medium such as aqueous ethanol or aqueous N,N-dimethylformamide at a temperature of from about 50° C. to about 100° C. Higher or lower temperatures appear to offer no advantages.

The required 2-chloro-4(3H)quinazolinones are, in turn, prepared by a reaction sequence beginning with the appropriately substituted o-aminobenzoic acid. The aminobenzoic acid reactant is converted to a ureido derivative by treatment with an alkali metal cyanate (e.g., KOCN, NaOCN) followed by cyclization of the ureido derivative under aqueous acid or base conditions as is described in U.S. Pat. No. 3,511,836, issued May 12, 1970.

Alternatively, the o-aminobenzoic acid can be reacted with urea according to the procedure of Curd et al., *J. Chem. Soc.*, 1947, page 777, to provide the same compound. The 2,4-(1H,3H)quinazolinedione is then reacted, as is described in U.S. Pat. No. 3,511,836, with a halogenating agent such as phosphorous oxychloride or a mixture thereof to give the 2,4-dichloroquinazoline. The 2,4-dichloro compound is then converted to the 2-chloro-4(3H)quinazolinone by hydrolysis according to known procedures with an aqueous alkali metal or alkaline earth hydroxide and preferably with sodium or potassium hydroxide. The conversion is conveniently carried out by reacting the dichloro compound with sodium or potassium hydroxide in tetrahydrofuran or other reaction-inert solvent.

The necessary o-aminobenzoic acid reactants, if not known compounds, are obtainable by methods known to those skilled in the art.

The products of this invention and the pharmaceutically-acceptable cationic salts thereof are useful for the control (prophylactic and therapeutic treatment) of peptic ulcers and as prophylactic agents to inhibit or prevent the release of mediators of anaphylaxis (allergy, immediate hypersensitivity reactions) and the occurrence of allergic symptoms in mammals, and can be administered for such uses individually or as mixtures with other agents; for example, with theophylline or sympathomimetic amines. They can be administered alone, but are generally administered with a pharmaceutical carrier selected on the basis of the chosen route of administration and standard pharmaceutical practice. For example, they can be combined with various pharmaceutically-acceptable inert carriers in the form of tablets, capsules, lozenges, troches, hard candies, powders, aerosol sprays, aqueous suspensions or solutions, injectable solutions, elixirs, syrups and the like. Such carriers include solid diluents or fillers, sterile aqueous media and various non-toxic organic solvents. Moreover, the oral pharmaceutical compositions of this invention can be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of standard pharmaceutical practice. For example, when the compounds of this invention are administered orally in tablet form, excipients such as lactose, sodium citrate, calcium carbonate and dicalcium phosphate can be used. Various disintegrants such as starch, alginic acids and certain complex silicates, together with lubricating agents such as magnesium stearate, sodium lauryl sulphate and talc, can also be used in producing tablets for the oral administration of these compounds. For oral administration in capsule form, lactose and high molecular weight polyethylene glycols are among the preferred materials for use as pharmaceutically-acceptable carriers. Where aqueous suspensions are to be used for oral administration, the compounds of this invention can be combined with emulsifying or suspending agents. Diluents such as ethanol, propylene glycol, glycerine and chloroform and their combinations can be employed as well as other materials.

For the purpose of parenteral administration and inhalation, solutions or suspensions of these compounds in sesame or peanut oil or aqueous propylene glycol solutions can be employed, as well as sterile aqueous solutions of the soluble pharmaceutically-acceptable salts described herein. These particular solutions are especially suited for intramuscular and subcutaneous injection purposes should such method of administration be desired. The aqueous solutions, including those of the salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

Having full regard for the foregoing factors, it is considered that an effective daily oral or intraperitoneal dosage of the compounds of the present invention in humans of from about 10 to about 1500 mg. per day, with a preferred range of about 10 to about 600 mg. per day in single or divided doses, or at about 0.2 to about 12 mg./kg. of body weight will effectively inhibit or prevent release of mediators of anaphylaxis in human subjects. These values are illustrative and there may, of course, be individual cases where higher or lower dose ranges are merited. With careful supervision, the dosage level can range up to as high as about 2 grams per day.

When administered intravenously or by inhalation, the effective daily dose is from about 0.05 to about 400 mg. per day, and preferably from about 0.25 to 200 mg. per day, or at about 0.005 to 4 mg./kg. of body weight in single or divided doses.

When used as prophylactic agents to prevent the release of mediators of anaphylaxis, the compounds can be administered by inhalation. Compositions suitable for inhalation can comprise (1) a solution or suspension of the active ingredient in a liquid medium of the type mentioned above for administration via a nebulizer; (2) a suspension or solution of the active ingredient in a liquid propellant such as dichlorodifluoromethane or chlorotrifluoroethane for administration from a pressurized container; or (3) a mixture of the active ingredient and a solid diluent (e.g., lactose) for administration from a powder inhalation device. Compositions suitable for inhalation by means of a conventional nebulizer will comprise about 0.1 to about 1% of active ingredient; and those for use in pressurized containers will comprise from about 0.5 to about 2% of active ingredient. Compositions for use as powder inhalants can comprise ratios of active ingredient to diluent of from about 1:0.5 to about 1:1.5.

It is necessary that the active ingredient form a proportion of the composition such that a suitable dosage form will be obtained. Obviously, several dosage unit forms can be administered at about the same time. Although compositions with less than 0.005% by weight of active ingredient might be used in certain instances, it is preferred to use compositions containing not less than 0.005% of the active ingredient; otherwise, the amount of carrier becomes excessively large. Activity increases with the concentration of the active ingredient. The composition may contain 10, 50, 75, 95 or an even higher percentage by weight of the active ingredient.

The effectiveness of the products of this invention as antiulcer agents is determined by the stressed rat assay as follows:

Cold-Restraint Stressed Rat

Non-fasted female rats (Charles River C-D strain) weighing 70-140 gms. are administered the drug or carrier (control animals) intraperitoneally (in saline solution containing 1% carboxymethylcellulose and 0.1% Tween 80) or orally (in water) three hours before being lightly anesthetized with ether and taped in the supine position to individual sheets of plexiglass. After recovery from the anesthesia, the restrained animals are positioned horizontally in a refrigerator maintained at 10°-12° C. and three hours later sacrificed by cervical dislocation. The abdomen of each rat is opened, the pylorus clamped, the stomach inflated with saline via an oral tube, the esophagus clamped and the stomach excised. The stomachs are placed in a 0.4% formaldehyde solution for approximately 30 seconds to harden the outer layers and facilitate examination. Each stomach is then cut open along the greater curvature and the glandular portion (hind stomach) examined for damage. The number of gastric erosions, their severity and the color of the stomachs is recorded. The Mann-Whitney-Wilcoxon rank sum test is used to compare the median number of gastric erosions in the control group with the median number of gastric erosions in each drug-treated group to determine if they are stastically different. (Dixon et al., "Introduction to Statistical Analysis," 3rd Ed., McGraw-Hill Book Company, New York, pp. 344-347, 1969).

Their effect on gastric acid output in pylorus-ligated (i.e., Shay) rats is determined by the following procedure.

Shay Rat

Forty-eight hours before surgery female rats (Charles River C-D strain; 100-140 gms.) are individually caged and taken off normal food. Each animal is given two sugar cubes and water ad libitum to effect emptying of the stomach. Drug or carrier is administered intraperitoneally and three hours later, under ether anesthesia, the abdomen is shaved and opened along the linea alba. After exposing and ligating the pylorus, the incision is closed and the animal is returned to its cage and allowed to regain consciousness. Three hours later the animal is sacrificed by cervical dislocation, the abdomen reopened, the distal esophagus clamped, and the stomach excised. The stomach is cut open and the contents washed into a beaker with one ml. of deionized water. The volume of gastric juice is recorded following centrifugation. Excessively dirty (greater than 0.5 ml. of solids) or bloody samples are discarded. The acidity of one ml. of gastric juice is determined by tritration with a standardized NaOH (0.1N) solution using phenolphthalein as an indicator and total acid output ($\mu$eqH+/100 gms. body weight/3 hours) is calculated. A non-paired $t$ test is used to compare the means of the control and tested groups. (Dixon et al., *Technometrics*, X, 83-98, 1968). Carbenoxolone at 40 mg./kg. body weight consistently reduced gastric acid output in the three-hour Shay rat. At 80 mg./kg., carbenoxolone significantly decreased acid output in the Shay rat.

The same two basic changes are present in cases of anaphylactic shock: (1) an increase in permeability of capillaries, and (2) contraction of smooth muscle. The increased capillary permeability is the result of antigen-antibody interaction. It, and smooth muscle contraction, can be observed and readily measured. This increase in capillary permeability forms the basis of the PCA test.

The PCA test is a measure of the anti-allergic (especially anti-asthmatic) activity of a compound. Compounds which inhibit a positive PCA test induced by the rat immunochemical counterpart of human immunoglobulin E (IgE), or reagin, are considered to have anti-allergic activity (C. Mota, *Ann. N.Y. Acad. Sci.*, 103, 264, 1963). (Reagin is primarily immunoglobulin E [IgE] and is the principal immunoglobulin responsible for allergic asthma, anaphylaxis, hay fever, food sensitivities and certain manifestations of drug sensitivities). Such compounds when administered to a sensitized subject, human or animal, prior to the time when the subject comes into contact with antigens or substances to which it is allergic, will prevent the allergic reaction which would otherwise occur. They, therefore, provide a method for the prophylactic treatment of allergy or anaphylactic reactions of a reagin mediated nature.

To put it another way, such compounds block the release of mediators resulting from the antigen-antibody (allergic) reaction as illustrated in the PCA test using rat homocytotropic antibody—a known correlate of human reaginic antibody. Inhibition of reaginic antigen-antibody reactions in rats, the test animal of the PCA test, is regarded as representative of inhibition of human reaginic antigen-antibody reactions which occur during allergic episodes.

The PCA reaction test procedure employed to evaluate the compounds of the present invention demonstrates an excellent correlation between activity for compounds in this test and their utility in the treatment of allergic asthma. The ability of agents to interfere with PCA reactions is measured in male Charles River Wistar rats, 170-210 g. Reaginic antiserum, rich in IgE antibodies is prepared according to Petillo et al., *Int. Arch. Allergy*, 44, 309 (1973). Hyperimmune antiserum rich in IgG antibodies to hen egg albumin is prepared according to Orange. et al., *J. Exptl. Med.*, 127, 767 (1968). Forty-eight hours prior to antigen challenge, the reaginic antiserum is injected intradermally (i.d.) into the shaved skin of a normal rat's back; five hours before challenge the hyperimmune antisera is similarly injected. At a third site 60 mcg. histamine dihydrochloride and 0.5 mcg. serotonin creatinine sulfate are injected i.d. just prior to antigen challenge as a check for antihistaminic, antiserotonin and unspecific types of blockage; the compounds of the instant invention or saline are then administered i.v. and immediately followed by the challenge of 5 mg. egg albumen and 2.5 mg. Evans' Blue dye in saline. In the case of oral administration Evans' Blue dye and egg albumen are given five minutes after administration of the drug. Thirty minutes later the animals are asphyxiated using chloroform and the skin of the back removed and reversed for observation. A score is assigned each injection site equal to the product of the diameter of the site in mm. and a grade of 0.1, 0.5, 1, 2, 3 or 4 proportional to intensity of dye coloration. The scores for a given injection site are summed for each group of 5 animals and compared to the saline treated controls. The difference is expressed as percent blockade due to the compound employed.

Compounds representative of those of the present invention are tested for antiallergy activity by the above-described procedure and the resulting activities are reported as the degree (%) of protection. Intal, disodium cromoglycate, a commercial antiallergy agent, is included for comparison.

The compounds tested are of the formula

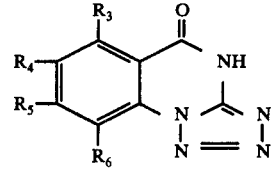

Intravenous and oral activity of compounds of this invention are presented in Tables I and II, respectively.

TABLE I:

| | | | | IgG I.V. (mg./kg.) | | | | | | | IgE I.V. (mg/kg.) | | | | | |
|---|---|---|---|---|---|---|---|---|---|---|---|---|---|---|---|---|
| $R_3$ | $R_4$ | $R_5$ | $R_6$ | 0.03 | 0.1 | 0.3 | 1 | 3 | 10 | 30 | 0.03 | 0.3 | 1 | 3 | 10 | 30 |
| H | H | H | H | | | 0 | 35 | 68 | 85 | 100 | | 8 | 9 | 77 | 91 | 100 |
| H | $OCH_3$ | H | H | | | | | 0 | | 96 | | | 20 | | | 46 |
| H | H | $OCH_3$ | H | | | 37 | 33 | 82 | 69 | | | 19 | 63 | 94 | 100 | |
| H | $OCH_3$ | $OCH_3$ | H | | | 3 | 1 | 32 | 52 | | | 9 | 34 | 83 | 89 | |
| H | $OC_2H_5$ | $OC_2H_5$ | H | | | 45 | | 72 | | | | 11 | | 83 | | |
| H | —O—$CH_2$—$CH_2$—O— | | H | 0 | | 56 | 76 | | | | 29 | 53 | | 93 | | |
| H | $OCH_3$ | $OC_2H_5$ | H | | | | | 75 | | | | | | 90 | | |
| H | $OCH_3$ | O—n-$C_3H_7$ | H | | 12 | 67 | 86 | 85 | | | 14 | 80 | 100 | 98 | | |
| H | $OCH_3$ | O—i-$C_3H_7$ | H | | 4 | 65 | | 77 | | | 0 | 78 | | 100 | | |
| H | $OCH_3$ | O—n-$C_4H_9$ | H | | 11 | 43 | | 62 | | | 0 | 78 | | 100 | | |
| H | H | O—n-$C_3H_7$ | H | | 0 | 0 | | 63 | | | 0 | 18 | | 100 | | |
| H | H | Cl | H | | | | 37 | 6 | 78 | | | | 0 | 55 | 86 | |
| H | Cl | H | H | | | | | | 11 | | | | | | 0 | 35 |
| H | H | H | Cl | | | | | 36 | | | | | | 11 | | |
| H | $CH_3$ | H | H | | | | | 32 | | | | | | 77 | | |
| H | H | $CH_3$ | H | | | | | 35 | | | | | | 22 | | |
| H | H | H | $CH_3$ | | | | | 41 | | | | | | 10 | | |
| $CH_3$ | H | H | $CH_3$ | | | | | 38 | | T* | | | | 28 | | T |
| H | H | $CH_3$ | $CH_3$ | | | | | 40 | | T | | | | 28 | | T |
| H | $CH_3$ | H | $CH_3$ | | | 18 | | 43 | T | | | | 77 | | T | |
| Intal | | | | | | | | | | | | 29 | 56 | 78 | 89 | 99 |

*Toxic

TABLE II:

| | | | | IgG P.O. mg./kg. | | | | | | IgE P.O. (mg./kg.) | | | | | |
|---|---|---|---|---|---|---|---|---|---|---|---|---|---|---|---|
| $R_3$ | $R_4$ | $R_5$ | $R_6$ | 0.3 | 1 | 3 | 10 | 30 | 100 | 0.3 | 1 | 3 | 10 | 30 | 100 |
| H | H | H | H | 19 | 33 | 42 | 66 | 73 | 89 | 10 | 10 | 23 | 48 | 62 | 73 |
| H | $OCH_3$ | H | H | | | | | 56 | | | | | | 78 | |
| H | H | $OCH_3$ | H | | 5 | 31 | 58 | 71 | | | 36 | 52 | 83 | 85 | |
| H | —O—$CH_2$—CH-—O— | | H | | | | 50 | 67 | | | | | 15 | 85 | |
| H | $OCH_3$ | $OC_2H_5$ | H | | | | 11 | | | | | | | 67 | |
| H | $OCH_3$ | O—n-$C_3H_7$ | H | 21 | 47 | 58 | 68 | 60 | | 35 | 63 | 82 | 85 | 81 | |
| H | $OCH_3$ | O—i-$C_3H_7$ | H | 0 | 21 | 50 | 49 | | | 0 | 38 | 70 | 81 | | |
| H | $OCH_3$ | O—n-$C_4H_9$ | H | | | 44 | | | | | | 90 | | | |
| H | H | O—n-$C_3H_7$ | H | | 0 | | 71 | | | | 0 | | 32 | | |
| H | $CH_3$ | H | H | | | | | 76 | | | | | | 64 | |

8,9-Dimethoxytetrazolo[1,5-c]quinazol-5(6H)-one, a compound described in U.S. Pat. No. 3,838,126, when tested in the PCA test, exhibited via the intravenous route of administration 18, 83 and 70% protection against anaphylaxis due to immunoglobulin G (IgG) at dose levels of 0.3, 3 and 30 mg./kg., respectively; and 21, 84 and 85% protection against anaphylaxis due to immunoglobulin E (IgE) at dose levels of 0.3, 3 and 30 mg./kg. Oral administration of this compound afforded 35 and 57% protection against anaphylaxis due to IgG at levels of 30 mg./kg. and 100 mg./kg., respectively; and 52 and 59% protection against anaphylaxis due to IgE at levels of 30 and 100 mg./kg., respectively.

EXAMPLE 1

6-Methoxy-7-propoxy-2,4(1H,3H)quinazolinedione

3-Propoxy-4-methoxy-2-aminobenzoic acid (6.2 g., 27mmole) was suspended in water (180 ml.) containing acetic acid (3.5 ml.) and potassium isocyanate solution (6.2 g. in 20 ml. water) added dropwise. The reaction was stirred at 30°–40° C. for 2 hours. Then, sodium hydroxide (55 g.) pellets were added slowly, keeping the temperature below 40° C. After addition was completed, the temperature of the reaction mixture was raised to 90° C. for 0.5 hour. It was then cooled, concentrated and hydrochloric acid was added dropwise keeping the temperature below 40° C. The resulting solid was filtered and washed with water. Yield = 5.0 g. (73%) m.p. 259°–261° C.

EXAMPLE 2

8-Methyl-2,4-(1H,3H)quinazolinedione

3-Methylanthranilic acid (15 g., 0.1 mole), urea (36 g., 0.6 mole) and phenol (86 g.) were mixed together and heated to reflux for three hours. The reaction was then allowed to cool to 100° C. and ethanol (75 ml.) added dropwise. The resulting solid was filtered and washed twice with cold ethanol to afford 13.2 g. (75% yield); m.p. 170° C.

EXAMPLE 3

The following compounds were prepared according to the procedures of Examples 1 and 2 from appropriate reactants.

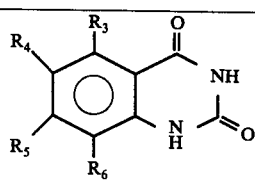

| $R_3$ | $R_4$ | $R_5$ | $R_6$ | Method | Yield (%) | M.P., ° C. |
|---|---|---|---|---|---|---|
| H | H | $OCH_3$ | H | 1 | 82 | 317° |
| H | | $-OCH_2-CH_2O-$ | H | 2 | 66 | 348° |
| H | $OCH_3$ | $OCH(CH_3)_2$ | H | 1 | 88 | 269° |
| H | H | H | $OCH_3$ | 2 | 76 | 255° |
| H | H | $CH_3$ | H | 2 | 36 | 320° |
| H | $CH_3$ | H | H | 1 | 96 | 316°(d) |
| H | $OCH_3$ | $OCH_2CH_3$ | H | 1 | 90 | 287° |
| H | H | $OCH_2CH_3$ | H | 2 | 38 | 290° |
| H | $CH_3$ | $CH_3$ | $CH_3$ | 2 | 85 | 328° |
| $CH_3$ | H | H | $CH_3$ | 2 | 90 | 290° |
| H | H | H | $CH_3$ | 2 | 50 | 300° |
| H | H | H | Cl | 2 | 68 | 321° |
| H | $OCH_3$ | $OCH_2CH_2CH_2CH_3$ | H | 2 | 76 | 228°–230° |
| H | H | $OCH_2CH_2CH_3$ | H | 2 | 63 | 261°–263° |
| H | $OCH_3$ | $OCH_2C_6H_5$ | H | 1 | 69 | 279°–281° |
| H | $OCH_2C_6H_5$ | $OCH_3$ | H | 1 | 46 | 240°–243° |

EXAMPLE 4

6-Methoxy-7-propoxy-2,4-dichloroquinazoline

6-Methoxy-7-propoxy-2,4-(1H,3H)quinazolinedione (4.95 g., 19.7 mM) was suspended in phosphorous oxychloride (60 ml.). The reaction was heated to reflux for 5 hours, then cooled and poured slowly onto 800 ml. of ice. The resulting orange-brown precipitate was filtered and washed twice with water and dried. Yield = 4.8 g. (86%); m.p. 118°–120° C.

EXAMPLE 5

Following the procedure of Example 4, the appropriate quinazolinediones are converted to the 2,4-dichloroquinazolines tabulated below.

| $R_3$ | $R_4$ | $R_5$ | $R_6$ | Yield (%) | m.p., ° C. |
|---|---|---|---|---|---|
| $CH_3$ | H | H | $CH_3$ | 72 | 125° |
| H | $CH_3$ | H | $CH_3$ | 45 | 153° |
| H | H | $CH_3$ | $CH_3$ | 33 | 142° |
| H | H | H | Cl | 40 | 125° |
| H | H | $CH_3$ | H | 90 | 107° |
| H | H | H | $CH_3$ | 80 | 137° |
| H | $CH_3$ | H | H | 64 | 144° |
| H | $OCH_3$ | $OCH(CH_3)_2$ | H | 92 | 190° |
| H | | $-OCH_2-CH_2O-$ | H | 50 | 225° |
| H | H | $OCH_3$ | H | 65 | 118° |
| H | $OCH_3$ | $OCH_2CH_3$ | H | 73 | 161° |
| H | H | H | $OCH_3$ | 90 | 156° |
| H | H | $OCH_2CH_2CH_3$ | H | 80 | 55° |
| H | $OCH_3$ | $OCH_2CH_2CH_2CH_3$ | H | 82 | 118°–120° |
| H | $OCH_3$ | $OCH_2C_6H_5$ | H | 34 | 160°–162° |
| H | $OCH_2C_6H_5$ | $OCH_3$ | H | 38 | 188°–191° |

EXAMPLE 6

6-Methoxy-7-propoxy-2-chloro-4(3H)quinazolinone

6-Methoxy-7-propoxy-2,4-dichloroquinazoline (4.5 g., 15.6 mmoles) was suspended in sodium hydroxide and tetrahydrofuran (30 ml.) and the reaction mixture stirred at room temperature for 36 hours until a clear solution resulted. Water (20 ml.) was added to the mixture which was then acidified with acetic acid to pH 5. The resulting solid was filtered and washed with water to yield 3.8 g. (90% yield) of the title monochloro compound; m.p. 246°–248° C.

EXAMPLE 7

The appropriate 2,4-dichloroquinazolines are converted to the corresponding 2-chloro-4(3H)quinazolines by the procedure of Example 6. The following compounds are thus prepared:

| $R_3$ | $R_4$ | $R_5$ | $R_6$ | Yield(%) | M.P., ° C. |
|---|---|---|---|---|---|
| CH$_3$ | H | H | CH$_3$ | 75 | 247° |
| H | CH$_3$ | H | CH$_3$ | 85 | 235° |
| H | H | CH$_3$ | CH$_3$ | 90 | 225° |
| H | H | H | Cl | 77 | 141° |
| H | H | H | CH$_3$ | 71 | 221° |
| H | H | CH$_3$ | H | 88 | 235° |
| H | CH$_3$ | H | H | 95 | 225° |
| H | OCH$_3$ | OCH$_2$CH$_2$CH$_2$CH$_3$ | H | 47 | 233–235° |
| H | OCH$_3$ | OCH(CH$_3$)$_2$ | H | 88 | 247° |
| H | —OCH$_2$—CH$_2$O— | | H | 88 | 282° |
| H | OCH$_3$ | OCH$_2$CH$_3$ | H | 83 | 269° |
| H | H | OCH$_2$CH$_2$CH$_3$ | H | 95 | 180° |
| H | H | OCH$_3$ | H | 85 | 240° |
| H | OCH$_2$CH$_3$ | OCH$_2$CH$_3$ | H | 89 | 221° |
| H | OCH$_2$C$_6$H$_5$ | OCH$_3$ | H | 88 | 254°–256° |
| H | H | H | OCH$_3$ | 87 | 195°–197° |

EXAMPLE 8

7-Methoxy-8-propoxy-tetrazolo[a]quinazol-5-one

6-Methoxy-7-propoxy-2-chloro-4(3H)quinazolinone (30 g., 11 mmoles) was suspended in a mixture of N,N-dimethylformamide (60 ml.), water (40 ml.) with sodium azide (0.8 g., 12 mmoles) and the mixture refluxed for 2 hours. After cooling, water (20 ml.) was added and the product which crystallized out was filtered, washed with water and dried. Recrystallization from N,N-dimethylformamide/water yielded 1.0 g. (33%) of the tetrazole, m.p., 244°–245° C.

Analysis: Calcd. for $C_{12}H_{13}N_5O_3$: C, 52.36; H, 4.76; N, 25.44; Found: C, 52.66; H, 4.96; N, 25.60.

EXAMPLE 9

By means of the procedure of Example 8, the tetrazolo[a]quinazol-5ones listed below are prepared from the appropriate 2-chloro-4(3H)quinazolinones.

| $R_3$ | $R_4$ | $R_5$ | $R_6$ | Yield(%) | M.P. (° C.) |
|---|---|---|---|---|---|
| H | H | H | H | 98 | 243° |
| H | CH$_3$ | H | H | 50 | 284–285° |
| H | H | CH$_3$ | H | 45 | 283–284° |
| H | H | H | CH$_3$ | 44 | 229–230° |
| CH$_3$ | H | H | CH$_3$ | 30 | 214–215° |
| H | CH$_3$ | H | CH$_3$ | 17 | 251–252° |
| H | H | CH$_3$ | CH$_3$ | 10 | 252–253° |
| H | H | H | Cl | 40 | 264–265° |
| H | OCH$_3$ | OCH(CH$_3$)$_2$ | H | 33 | 264–265° (d) |
| H | —OCH$_2$—CH$_2$O— | | H | 80 | 291–292° (d) |
| H | H | OCH$_2$CH$_2$CH$_3$ | H | 42 | 231–232° |
| H | H | OCH$_3$ | H | 67 | 271–272° |

-continued

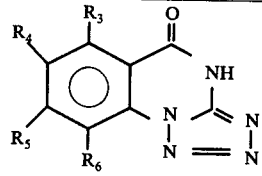

| $R_3$ | $R_4$ | $R_5$ | $R_6$ | Yield(%) | M.P. (° C.) |
|---|---|---|---|---|---|
| H | OCH$_2$CH$_3$ | OCH$_2$CH$_3$ | H | 76 | 245–246° |
| H | OCH$_3$ | OCH$_2$CH$_3$ | H | 25 | 264–265° |
| H | OCH$_3$ | OCH$_3$ | H | 57 | 249–250° |
| H | OCH$_3$ | OCH$_2$CH$_2$CH$_2$CH$_3$ | H | 57 | 233–234° |
| H | OCH$_3$ | H | H | 60 | 264–265° |
| H | Cl | H | H | 75 | 268–369° (d) |
| H | H | Cl | H | 80 | 340° |
| H | OCH$_2$C$_6$H$_5$ | OCH$_3$ | H | 13 | 260°–261° (d) |

EXAMPLE 10

The following compounds are prepared from appropriately substituted benzoic acids by the procedures of Examples 1, 4, 6, and 8.

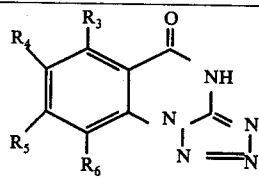

| $R_3$ | $R_4$ | $R_5$ | $R_6$ | $R_3$ | $R_4$ | $R_5$ | $R_6$ |
|---|---|---|---|---|---|---|---|
| H | H | n-C$_4$H$_9$ | H | H | H | H | I |
| H | H | sec-C$_4$H$_9$ | H | H | H | —O—CH$_2$—O— | |
| H | H | t-C$_4$H$_9$ | H | F | F | H | H |
| H | H | C$_2$H$_5$ | H | H | SO$_2$NH$_2$ | H | H |
| t-C$_4$H$_9$ | H | t-C$_4$H$_9$ | H | H | SO$_2$NH$_2$ | H | H |
| H | O-i-C$_3$H$_7$ | O-i-C$_3$H$_7$ | H | H | H | SO$_2$NH$_2$ | H |
| OCH$_3$ | H | OCH$_3$ | H | H | Cl | SO$_2$NH$_2$ | H |
| H | OCH$_3$ | H | OCH$_3$ | H | SO$_2$NH$_2$ | Cl | H |
| Br | H | H | H | H | OH | OCH$_3$ | H |
| H | Br | H | H | H | H | OH | H |
| H | H | Br | H | H | H | H | OH |
| Cl | H | H | Br | H | OC$_3$H$_7$ | OCH$_3$ | H |
| Br | H | H | H | H | H | OC$_3$H$_7$ | H |
| Br | Br | H | H | H | H | H | OC$_3$H$_7$ |
| Br | H | Br | H | H | OCH$_3$ | OH | H |
| H | H | Br | Cl | OC$_3$H$_7$ | H | OC$_3$H$_7$ | H |
| I | H | H | H | H | H | CF$_3$ | H |
| H | I | H | H | | | | |
| I | H | I | H | | | | |
| OCOCH$_3$ | H | OCOCH$_3$ | H | | | | |
| H | CF$_3$ | H | H | | | | |
| H | OCH$_3$ | OCH$_2$C$_6$H$_5$ | H | | | | |
| H | OC$_3$H$_7$ | OCH$_2$C$_6$H$_5$ | H | | | | |

EXAMPLE 11

7-Hydroxy-8-methoxytetrazolo[a]quinazol-5-one

7-Benzyloxy-8-methoxytetrazolo[a]quinazol-5-one (0.05 g.) is dissolved in trifluoroacetic acid (2 ml.) and the solution refluxed for 1.5 hours. The reaction mixture is cooled to room temperature and ether (4 ml.) is added. The resulting solid is filtered off, washed with ether (2 × 4 ml.) and air dried. The product is recrystallized from N,N-dimethylformamide-water (1–1). Yield = 0.025 g. (48%). M.P. >400° C.

In like manner, 7-methoxy-8-benzyloxytetrazolo[a]quinazol-5-one is debenzylated to the corresponding 8-hydroxy compound as the trifluoroacetate salt.

Neutralization of the above salts with sodium or potassium hydroxide in water affords the base form.

EXAMPLE 12

7-Acetoxy-8-methoxytetrazolo[a]quinazol-5-one Tosylate

A mixture of 7-hydroxy-8-methoxytetrazolo[a]-quinazol-5-one trifluoroacetate (0.01 g.), acetic anhydride (3 ml.) and p-toluenesulfonic acid (0.005 g.) is heated at 100° C. for 4 hours. The reaction mixture is cooled and evaporated to dryness under reduced pressure. The residue is dissolved in chloroform, decolorized, filtered and the filtrate evaporated to dryness under reduced pressure. The residue crystallizes upon addition of ether.

Neutralization in aqueous NaOH affords the base.

In like manner, the following compounds are prepared from appropriate alkanoic acid anhydrides and the products of Example 11.

| R₄ | R₅ | R₄ | R₅ |
|---|---|---|---|
| OCOH | OCH₃ | OCH₃ | OCOH |
| OCOC₂H₅ | OCH₃ | OCH₃ | OCOCH₃ |
| OCOC₃H₇ | OCH₃ | OCH₃ | OCOC₃H₇ |

EXAMPLE 13

Injectable Preparation

One thousand grams of 7-methoxy-8-n-propoxy tetrazolo[a]quinazol-5-one are intimately mixed and ground with 2500 grams of sodium ascorbate. The ground, dry mixture is placed in vials and sterilized with ethylene oxide after which the vials are sterilely stoppered. For intravenous administration, sufficient water is added to the materials in the vials to form a solution containing 5.0 mg. of active ingredient per milliliter of injectable solution.

EXAMPLE 14

Tablets

A tablet base is prepared by blending the following ingredients in the proportion by weight indicated:
Sucrose, U.S.P.:80.3
Tapioca Starch:13.2
Magnesium Stearate:6.5
Into this tablet base there is blended sufficient 7-methoxy-8-n-propoxytetrazolo[a]quinazol-5-one to provide tablets containing 20, 100, and 250 mg. of active ingredient per tablet. The compositions are each compressed into tablets, each weighing 360 mg., by conventional means.

EXAMPLE 15

Capsules

A blend is prepared containing the following ingredients:
Calcium carbonate, U.S.P.:17.6
Dicalcium phosphate:18.8
Magnesium trisilicate, U.S.P.:5.2
Lactose, U.S.P.:5.2
Potato starch:5.2
Magnesium stearate A:0.8
Magnesium stearate:0.35
To this blend is added sufficient 7-methoxy-8-isopropoxytetrazolo-[a]quinzol-5-one to provide capsules containing 10, 25 and 50 mg. of active ingredient per capsule. The compositions are filled into conventional hard gelatin capsules in the amount of 350 mg. per capsule.
In like manner, capsules containing 2.0 mg. and 6.0 mg. of active ingredient, and having 300 mg. of the following blends per capsule are prepared:

| Ingredients | Weight mg./capsule |
|---|---|
| Drug | 2.00 |
| N-methylglucamine | 18.00 |
| Lactose, anhydrous | 241.20 |
| Corn starch, anhydrous | 30.00 |
| *Talc | 8.80 |

-continued

| Ingredients | Weight mg./capsule |
|---|---|
| Drug | 6.00 |
| N-methylglucamine | 18.00 |
| Lactose, anhydrous | 237.20 |
| Corn starch, anhydrous | 30.00 |
| *Talc | 8.80 |

*Talc added before encapsulation

EXAMPLE 16

Solution

A solution of 8-n-propoxytetrazolo[a]quinazol-5-one is prepared with the following composition:
Effective ingredient:6.04 grams
Magnesium chloride hexahydrate:12.36 grams
Monoethanolamine:8.85 ml.
Propylene glycol:376.00 grams
Water, distilled:94.00 ml.

The resultant solution has a concentration of effective ingredient of 10 mg./ml. and is suitable for parenteral and, especially, for intramuscular administration.

EXAMPLE 17

An aqueous solution of 7-methoxy-8-n-propoxytetrazolo[a]quinazol-5-one (containing 3 mg. of drug per ml. of solution) is placed in a standard nebulizer such as is available from the Vaponephrine Co., Edison, N.J. The solution is sprayed under an air pressure of 6 lbs. per square inch into a closed 8 inches × 8 inches × 12 inches plastic container for six minutes. The container has four openings to accomodate the heads of four rats. Four rats are exposed to the drug simultaneously with only their heads coming in contact with aerosol. The results are evaluated as per the PCA reaction test procedure described above.

EXAMPLE 18

Aerosol Suspension

A mixture of 7-methoxy-8-n-propoxytetrazolo[a]-quinzaol-5-one (anti-allergy agent) and the other ingredients under (a) in the examples below are micronized to a particle size of 1 to 5 microns in a ball mill. The resulting slurry is then placed in a container equipped with a valve and propellant (b) introduced by pressure filling through the valve nozzle to a gauge pressure of approximately 35–40 pounds per square inch at 20° C.

| Suspension A | Percent |
|---|---|
| (a) Antiallergy agent | 0.25 |
| Isopropyl myristate | 0.10 |
| Ethanol | 26.40 |
| (b) 60–40% mixture of 1,2-dichlorotetrafluoro-ethane-1-chloropentafluoroethane | 73.25 |
| Suspension B | |
| (a) Antiallergy agent | 0.25 |
| Ethanol | 26.50 |
| (b) A 60-40% mixture of 1,2-dichlorotetrafluoroethane-1-chloropentafluoroethane | 73.25 |

What is claimed is:

1. A compound of the formula:

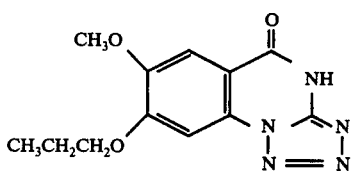

2. A method of inhibiting the release of mediators of anaphylaxis in a mammalian subject which comprises administering orally, intranasally, parenterally or by inhalation to the subject an anaphylaxis mediator release inhibiting amount of a compound having the formula:

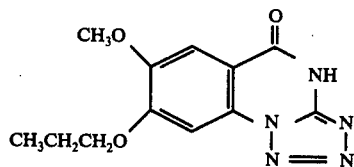

3. A composition suitable for inhibiting the release of mediators of anaphylaxis in a mammalian subject which comprises a unit dosage amount of the compound of claim 1 in a mixture with a pharmaceutically acceptable carrier.

* * * * *

UNITED STATES PATENT AND TRADEMARK OFFICE
CERTIFICATE OF CORRECTION

PATENT NO. : 4,085,213
DATED : April 18, 1978
INVENTOR(S) : Jasjit S. Bindra

It is certified that error appears in the above-identified patent and that said Letters Patent are hereby corrected as shown below:

Col. 15, lines 2-7, that portion of the formula reading

" 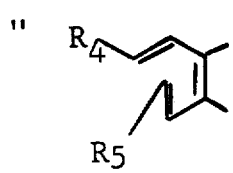 "  should read -- 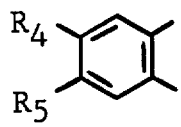 --.

Signed and Sealed this

Twenty-ninth Day of August 1978

[SEAL]

Attest:

RUTH C. MASON
Attesting Officer

DONALD W. BANNER
Commissioner of Patents and Trademarks